(12) United States Patent
McNamara et al.

(10) Patent No.: US 7,846,424 B2
(45) Date of Patent: *Dec. 7, 2010

(54) NON-PRESSURIZED POST-APPLICATION EXPANDING COMPOSITION

(75) Inventors: William E. McNamara, Middletown, NY (US); Derrick B. McKie, Brooklyn, NY (US); John S. Kurek, Goshen, NY (US); Clifford A. Milow, Monroe, NY (US); Mark S. Garrison, Suffern, NY (US); Raymond Cen, Belle Mead, NJ (US)

(73) Assignee: Avon Products, Inc, New York, NY (US)

( * ) Notice: Subject to any disclaimer, the term of this patent is extended or adjusted under 35 U.S.C. 154(b) by 1279 days.

This patent is subject to a terminal disclaimer.

(21) Appl. No.: 10/532,361

(22) PCT Filed: Dec. 19, 2003

(86) PCT No.: PCT/US03/40790

§ 371 (c)(1), (2), (4) Date: Apr. 20, 2005

(87) PCT Pub. No.: WO2004/060292

PCT Pub. Date: Jul. 22, 2004

(65) Prior Publication Data

US 2006/0147399 A1    Jul. 6, 2006

Related U.S. Application Data

(63) Continuation-in-part of application No. 10/331,069, filed on Dec. 27, 2002.

(51) Int. Cl.
  *A61Q 1/10* (2006.01)
  *A61Q 5/00* (2006.01)

(52) U.S. Cl. ............ 424/70.7; 424/70.11; 424/70.19; 424/70.21; 424/70.22

(58) Field of Classification Search .............. None
See application file for complete search history.

(56) References Cited

U.S. PATENT DOCUMENTS

| | | |
|---|---|---|
| 2,995,521 A | 8/1961 | Estiguard-Bluard |
| 3,541,581 A | 11/1970 | Monson |
| 3,654,167 A | 4/1972 | Akrongold et al. |
| 3,876,771 A | 4/1975 | Denner |
| 4,405,489 A | 9/1983 | Sisbarro |
| 4,528,111 A | 7/1985 | Su |
| 4,651,503 A | 3/1987 | Anderson, III et al. |
| 5,334,325 A | 8/1994 | Chaussee |
| 5,389,363 A * | 2/1995 | Snyder et al. ............ 424/70.7 |
| 5,523,081 A | 6/1996 | Edwards et al. |
| 5,571,794 A | 11/1996 | Frome |
| 5,623,017 A | 4/1997 | Hill |
| 5,683,625 A | 11/1997 | Derthiaume et al. |
| 5,705,562 A | 1/1998 | Hill |
| 5,800,825 A | 9/1998 | McMullen |
| 5,962,396 A | 10/1999 | Pollack et al. |
| 6,027,738 A | 2/2000 | Stepniewski et al. |
| 6,030,630 A | 2/2000 | Fleury et al. |
| 6,051,542 A | 4/2000 | Pollack et al. |
| 6,096,702 A * | 8/2000 | Ramirez et al. ............ 510/421 |
| 6,117,435 A | 9/2000 | Painter et al. |
| 6,165,456 A | 12/2000 | Barnet et al. |
| 6,177,092 B1 | 1/2001 | Lentini et al. |
| 6,224,851 B1 | 5/2001 | Bara |
| 6,251,375 B1 | 6/2001 | Bara |
| 6,299,890 B1 | 10/2001 | Russ et al. |
| 6,328,950 B1 | 12/2001 | Franzke et al. |
| 6,440,430 B1 | 8/2002 | Bara et al. |
| 6,440,923 B1 | 8/2002 | Lyle et al. |
| 6,524,594 B1 | 2/2003 | Santora et al. |

(Continued)

FOREIGN PATENT DOCUMENTS

| | | |
|---|---|---|
| EP | 1216684 A1 | 6/2002 |
| JP | 07-53325 A | 2/1995 |
| JP | 08-73839 A | 3/1996 |
| JP | 52-5683 A | 1/1997 |
| JP | 09-77629 A | 3/1997 |
| JP | 10279453 A | 10/1998 |
| JP | 2003-201217 A | 7/2003 |
| WO | WO 96/19189 | 6/1996 |
| WO | WO 98/20096 | 5/1998 |
| WO | 03/043598 A1 | 5/2003 |

(Continued)

OTHER PUBLICATIONS

U.S. Appl. No. 10/331,069, filed Dec. 27, 2002, W. McNamara et al.
U.S. Appl. No. 10/532,362, filed Apr. 20, 2005, W. McNamara et al.
Database WPI Week 199722 Thomson Scientific, London, GB: AN 1997-241614; AP002515877 & JP 09077629 A (Mandom KK) Mar. 25, 1997 *abstract*.

*Primary Examiner*—Jyothsna A Venkat
(74) *Attorney, Agent, or Firm*—Charles J. Zeller; Joan M. McGillycuddy; Anthony M. Santini

(57) ABSTRACT

A post-application expanding composition for application to hair fibers of the scalp, eyebrows or eyelashes is provided. The composition comprises at least one surfactant, a solvent for the surfactant, and a volatile agent in an amount that will cause the surfactant and solvent to interact and foam on the hair fibers thereby producing an expanded composition. The composition further contains a film-forming agent in an amount effective to form a film which when set fixes at least a portion of the expanded composition in its expanded state. The volatile agent is solubilized in the composition, and is further dispersed throughout the composition in nanometer size droplets or generated in situ on the hair fibers or immediately prior to application thereto so that the composition is storable in a non-pressurized container.

30 Claims, No Drawings

U.S. PATENT DOCUMENTS

| | | |
|---|---|---|
| 6,579,907 B1 | 6/2003 | Sebillotte-Arnaud et al. |
| 6,607,734 B1 | 8/2003 | Afriat |
| 2002/0122772 A1 | 9/2002 | Lukenback et al. |

FOREIGN PATENT DOCUMENTS

| | | |
|---|---|---|
| JP | 03-31389 A | 2/1991 |
| JP | 03-178923 A | 8/1991 |

* cited by examiner

NON-PRESSURIZED POST-APPLICATION EXPANDING COMPOSITION

This application is a continuation-in-part of application Ser. No. 10/331,069, filed Dec. 27, 2002.

BACKGROUND OF THE INVENTION

1. Field of the Invention

The present invention is based on the finding that a post-application expanding composition for application to hair fibers of the scalp, eyebrows or eyelashes, which utilizes (a) the vaporization of a volatile (blowing) agent component of the composition to expand surfactant and solvent components of the composition, and (b) a film-forming agent component of the composition that sets and fixes at least a portion of the composition in its expanded state so as to impart a volumizing effect to the hair fibers, can be based on (i) a micro-emulsion system, (ii) a system for solubilizing the volatile agent in the composition or (iii) a system in which the volatile (blowing) agent is carbon dioxide generated in situ on the hair fibers.

Advantageously, post-application expanding compositions based on a micro-emulsion system, a system in which the volatile agent is solubilized in the composition or a system in which carbon dioxide is generated in situ on the hair fibers or just prior to application thereto, can be stored in non-pressurized containers thereby greatly reducing manufacturing and packaging cost and facilitating use of the compositions.

2. Description of the Related Art

Numerous microemulsion based products are know in the art. Such products include rigid polyurethane insulation foams, industrial surface cleansers, shaving compositions and silicone microemulsions for use in personal care.

U.S. Pat. Nos. 5,962,396 and 6,051,542 disclose a post-foaming cleaning composition utilizing hydrocarbon blowing agents and requiring packaging in a pressurized container. There is no appreciation of the use of a microemulsion to arrest a blowing agent.

U.S. Pat. No. 5,523,081 discloses polyorganosiloxane microemulsion based shave creams. The smaller particle size of the microemulsion is said to provide enhanced lubrication, richness and stability of the shave foam. There is however no appreciation of arresting a volatile agent through use of a microemulsion, nor is there any mention of pigment or film former(s).

U.S. Pat. No. 5,623,017 discloses an optically clear silicone microemulsion system containing cyclic or linear methyl siloxanes and a silicone polyether surfactant. The clear gel is said to be useful as a carrier in antiperspirants and deodorants, skin creams, skin care lotions, moisturizers, facial treatments such as acne or wrinkle removers, personal and facial cleansers, liquid soaps, bath oils, perfumes, colognes, sachets, sunscreens, pre-shave and after-shave lotions, shaving soaps, and shaving lathers. Patentee also indicates that the clear gel can be used in shampoos, conditioners, hair sprays, mousses, permanents, depilatories, and cuticle coats. Patentee also states that the clear gel can be used as a leveling and spreading agent for pigments in make-ups, color cosmetics, foundations, blushes, lip balms, eyeliners, mascaras, oil removers, color cosmetic removers, and powders. There is no appreciation whatsoever of the use of a microemulsion to arrest a volatile (blowing) agent in a post-application expanding composition.

U.S. Pat. No. 5,705,562 describes a spontaneously formed clear silicone microemulsion. The purpose of the microemulsion is for leveling and spreading pigments, not for arresting a volatile agent in a post-application expanding composition.

U.S. Pat. No. 5,683,625 discloses transparent microemulsion compositions that contain low amino content microemulsifiable silicones and have high phase inversion temperatures. The microemulsion can be a component of personal care product formulations such as hair conditioners and shampoos, and hair fixatives such as styling gels and mousses.

U.S. Pat. No. 6,096,702 discloses post-foaming detergent compositions containing a polyalkylene oxide block copolymer surfactant which in the presence of anionic and amphoteric detergents solubilizes a volatile hydrocarbon producing a clear solution or gel useful as a skin cleanser, hair shampoo, shower gel, spot cleanser for clothes, carpet cleaner or hard surface cleaner. Patentees indicate that the "resulting clear, instant foaming liquid or gel will foam on a surface with or without the aid of water" (emphasis supplied) and "can be packaged in an unpressurized container such as bottle and pumps or in pressurized aerosol packages when n-butane, isobutene or dimethylether propellant is used." Patentees also disclose compositions containing ammonium cocoyl isethionate in combination with an amphoteric surfactant are extremely mild, making them particularly useful in skin and hair care compositions. Patentees also teach that the combination of ammonium cocoyl isethionate with amphoteric surfactants will solubilize volatile hydrocarbons to produce clear post-foaming solutions without the aid of any ethoxylated, propoxylated or mixed block polymer. Patentees in characterizing the compositions of the '702 patent as "instant foaming" clearly do not teach or even suggest a composition wherein foaming is delayed. Patentees indicate that their compositions can contain a variety of non-essential ingredients. Water soluble gums such as cellulosic polymers or natural gum, are disclosed to be non-essential ingredients. Thus, patentees clearly fail to appreciate the necessity of including in their composition a film-forming agent in an amount sufficient to entrap at least a portion of the foam lattice produced when the volatile agent interacts with the surfactant and solvent for the surfactant (viz water) and thereby provide a volumizing effect to the hair fibers. Although patentees indicate that color can be added to improve the cosmetic appearance of the product, they do not appreciate the use of color in an amount sufficient to impart a color other than white to hair of the scalp, eyebrows or eyelashes.

The in situ reaction of an acid with a carbonate or bicarbonate to produce carbon dioxide is well known in the art.

However, post-application expanding compositions, for application to the hair of the scalp, eyebrows or eyelashes, that utilize in situ generated carbon dioxide to foam one or more surfactant components of the composition and a film-forming component of the composition to entrap at least a portion of the foam lattice and, when set, fix the composition in an expanded state, have not heretofore been appreciated by the prior art.

PCT International Publication No. WO 96/19189 utilizes the reaction of a carbonate or bicarbonate with an acid to produce immediate intensive foam formation in a dental hygiene product. The inventors seek rapid foaming, not delayed foaming.

Japanese Patent Publication No. 10279453A discloses a tooth powder composition for plaque removal. The composition contains a carbonate or bicarbonate, an acid and a surfactant. The Abstract contains no mention of the presence of a film forming agent or of the composition being a post-foaming composition.

The aforementioned PCT and Japanese prior art citations fail to teach inclusion of a film-forming agent or delayed foam production (post-foaming). More importantly, they fail to teach or suggest that their compositions can be applied to the hair of the scalp, eyebrows or eyelashes.

PCT International Publication No. WO 98/20096 teaches a denture cleanser that effervesces rapidly and is not post-foaming.

U.S. Pat. No. 6,177,092 discloses a self-foaming cleansing system for application to the skin or hair. The system has at least two components maintained in separate containers. When dispensed from their separate containers they mix and react to produce carbon dioxide. Patentees teach the desirability of effervescence immediately upon contact. Thus, the compositions of the '092 patent are not delayed/post-foaming compositions. Moreover, patentees do not appreciate the use of a film-forming agent in an amount sufficient so that when it sets it entraps at least a portion of the foam produced by action of the in situ generated carbon dioxide on the surfactant components of the composition.

SUMMARY OF THE INVENTION

The present invention obviates the need for storing the post-application expanding composition in a pressurized container. In other words, the present invention makes unnecessary the use of a barrier type container capable of withstanding the pressure required to hold the volatile (blowing) agent component of the composition dispersed in the composition.

The present invention accomplishes this by solubilizing the volatile (blowing agent) of the composition through (i) use of a primary solubilizing agent (a polymer surfactant (a block copolymer), polyvinyl alcohol, a polyvinyl alcohol alternative or a mixture thereof); or (ii) use of a micro-emulsion or (iii) by dividing the composition into at least two separate subcompositions, one containing a bicarbonate or carbonate salt, the other containing a cosmetically acceptable acid or one containing the bicarbonate or carbonate salt and the acid dispersed or suspended in an anhydrous vehicle and the other containing water. When the subcompositions are mixed on the hair fibers or just prior to application to the hair fibers, the bicarbonate or carbonate salt will react with the acid to produce carbon dioxide which in turn will expand (foam) the surfactant and solvent for the surfactant, on the hair fibers.

DETAILED DESCRIPTION OF THE INVENTION

The present invention provides three embodiments ((i), (ii) and (iii)), discussed immediately above, for obviating the necessity for storing the post-application expanding composition in a pressurized container. For convenience sake these embodiments are referred to as the:

(1) "Solubilization System";
(2) "Microemulsion System" (microemulsion based composition); and the
(3) "Two Part System" (two part composition employing in situ generated carbon dioxide as the volatile agent).

The Solubilization System, Microemulsion System and Two Part System all contain as a component thereof: a film forming agent, a surfactant, a solvent for the surfactant, and, optionally, a colorant.

The Solubilization and Microemulsion Systems also contain a volatile (blowing agent). In the Two Part System, the volatile (blowing) agent is carbon dioxide generated in situ.

As noted earlier, all three systems contain a surfactant. When the volatile agent is released, it interacts with the surfactant and solvent for the surfactant (for example, water) to produce a foam lattice. Thus, the surfactant serves to generate foam. In contrast thereto, in the Solubilization System, the primary solubilizing agent, for example, the block copolymer surfactant, functions primarily to solubilize the volatile agent. In addition to solubilizing the volatile agent, the block copolymer surfactant may also be capable of generating a foam lattice. This is secondary to its primary function as a solubilizer for the volatile agent. Additional surfactant(s) are preferably employed along with the block copolymer surfactant to boost foam production and/or increase foam density and/or produce a more stable foam.

Film-Forming Agent

The film forming agent is present in an amount sufficient so that when the post-application expanding composition is applied to the hair of the scalp, eyebrows or eyelashes, and the post-foaming component begins to foam, the film formed by the film forming agent will stabilize at least a portion of the foam (as will be elaborated on more fully below) thereby imparting a volumizing effect to the hair fibers upon which the composition of the invention is applied.

The film forming agent can be natural or synthetic. Film forming waxes are known in the art and can be employed alone or in combination with one or more natural or synthetic film forming agents. Synthetic film forming agents, for example, acrylates copolymers and/or methacrylates copolymers, acrylamide copolymers, and mixtures thereof, are particularly preferred.

Water-soluble film forming agents that can be utilized are exemplified in monographs 27-33 of the International Cosmetic Ingredient Dictionary and Handbook, $9^{th}$ Ed. (2002). Particularly preferred film formers include; (i) acrylamide copolymer; for example, acrylamides/DMAPA acrylates/methoxy PEG methacrylate copolymer, acrylamide/sodium acrylate copolymer, acrylamide/sodium acryloyldimethyltaurate copolymer, acrylates/acrylamide copolymer, acrylates/t-butylacrylamide copolymers and (ii) acrylates copolymer, for example, BF Goodrich's AVALURE AC115, AVALURE AC118, AVALURE AC120, AVALURE AC125, AVALURE AC210 and AVALURE AC315; LCW's COVACRYL A15 and COVACRYL E14; Daito Kasei's DAITOSOL 5000 AD; acrylates/C1-2 succinates/hydroxyacrylates copolymer; acrylates/dimethicone copolymer; acrylates/dimethicone methacrylate/ethylhexyl acrylate copolymer; acrylates/dimethylaminoethyl methacrylate copolymer; acrylates/ethylhexyl acrylate copolymer; acrylates/ethylhexylacrylate/HEMA/styrene copolymer; acrylates/hydroxyesters acrylates copolymer; acrylates/laurylacrylate/stearyl acrylate/ethylamine oxide methacrylate copolymer; acrylates/octylacrylamide copolymer; acrylates/propyl trimethicone methacrylate copolymer; acrylates/stearyl acrylate/dimethicone methacrylate copolymer; acrylates/VP copolymer; and acrylates/VP/dimethylaminoethyl methacrylate/diacetone acrylamide/hydroxypropyl acrylate copolymer. Polyvinyl alcohol and water-soluble polyvinyl esters can also be employed.

More preferred film-forming agents useful in the present invention include sodium acrylates copolymer, sodium acryloldimethyl taurate copolymer, ethyl methacrylate/N-butyl acrylate/2-methylhexyl acrylate copolymer, and butyl acrylate/hydroxyethyl methacrylate copolymer. Polymeric blends, such as Interpolymer's SYNTRAN EX-100 and Kobo Product's DAITOSOL 5000 SJ are also useful as synthetic polymer film forming agent in the composition of the present invention.

Depending on whether the post-application expanding composition of the present invention is mostly water or mostly oil, an appropriate film forming agent can be utilized. In point of fact, when the post-expanding composition is an emulsion, either a water-soluble film forming agent, or an oil-soluble film forming agent, or both, can be employed.

When the post-expanding composition is mostly oil (either organic or synthetic), an oil-soluble synthetic polymer can employed as the film forming agent. Suitable oil-soluble synthetic polymers include, for example, polyurethane-1, polyurethane-2, polyurethane-3, polyurethane-4, polyurethane-5, polyurethane-6, polyurethane-7, polyurethane-8, polyurethane-9, polyurethane-10, polyurethane-11, polyethylene, oxidized polyethylene, polypropylene, tetramethyl tetraphenyl trisiloxane, tricontanyl trimethyl pentaphenyl trisiloxane, styrene/MA copolymer, styrene/DVB copolymer, various quaternary ammonium synthetic polymers, and crosspolymer, such as PVM/MA decadiene crosspolymer.

Various oil-soluble derivatives of polyvinyl pyrrolidone copolymers can also be used, with polyvinylpyrrolidone/decene copolymer and poly (vinyl pyrrolidone/1-triacontene) being preferred. The ethyl ester of PVM/MA copolymer can be used as well.

Water-soluble polyurethanes can also be used as the film forming agent, for example, EPQ 30 and EPQ 31 (Johnson Polymers) and the polyester urethane GK 910 (ALZO International, Inc.).

Preferably, the film forming agent is present in the post-application expanding composition of the invention in a concentration from about 1 to about 50% by weight, more preferably about 5 to about 40% by weight, most preferably about 8 to about 30% by weight, and optimally about 10 to about 25% by weight, based on the total weight of the post-application expanding composition.

When the post-expanding composition of the present invention is applied on hair fibers, such as the eyelashes, the volatile agent will release and cause the surfactant and solvent for the surfactant to swell/expand the composition. When the film forming agent sets, it fixes at least a portion of the swelled/expanded composition on the eyelashes in its swelled/expanded state, thereby imparting a volumizing effect to the eyelashes.

As will be discussed below, the composition of the present invention may contain a pigment dispersion that includes one or more film forming agents. The amount of film forming agent contributed by the pigment dispersion is considered in the total amount of film forming agent in the post-application expanding composition. For example, if the post-application expanding composition contains 50 wt %, based on the total weight of the composition, of a pigment dispersion that further contains 40 wt %, based on the total weight of the pigment dispersion, of a film forming agent, the composition of the invention has 20 wt %, based on the total weight of the composition, film forming agent (due to the contribution of the pigment dispersion). Additional film forming agent may be added. However, from a cost standpoint it is preferred that the total not exceed about 50 wt %, based upon the total weight of the composition.

While the present inventors do not wish to be bound to any one theory, it is believed that during the post-foaming action the film forming agent will set, thus, locking or sealing the foam lattice in place, either by forming a film, preferably a flexible film, over at least a portion of the surface of the foam or by increasing the rigidity of the foam lattice thereby stabilizing the foam. Preferably, a film will form over greater than about 50 percent of the surface of the foam, and more preferably over greater than about 75 percent of the surface of the foam. Alternatively, the film forming agent increases the rigidity of the foam lattice by greater than about 50%, and more preferably by greater than about 75%.

Since the compositions of the present invention are preferably used as cosmetic compositions for application to the skin of the lips or face, it is preferred that the film forming agent is of the type and amount to allow the composition to be removed from the user with water, mild soap or a mild cosmetic cleanser. Where water washability/rinseability is not required, a non-water-soluble film forming agent can of course be employed.

Volatile Agent

Suitable volatile or blowing agent(s) (halogenated or non-halogenated, synthetic or naturally occurring) have a vapor pressure from about 0.5 Torr to about 30,000 Torr, preferably from about 5.0 Torr to about 5,000 Torr, and more preferably, from about 100 Torr to about 2,500 Torr, at a temperature of about 0° to about 100° C.

Examples of preferred volatile agents include, but are not limited to, n-pentane, isopentane, neopentane, n-butane, isobutane, isobutene, cyclopentane, hexane, trichlorotrifluorethane, 1,2-dichloro, 1,1,2,2-tetrafluoroethane, hydrofluoroethers, methyl perfluoropropyl ether and mixtures thereof. Other suitable volatile agents may include, but are not limited to, perfluoromethylcyclohexane, manufactured by F2 Chemicals Ltd. under the trade name Flutec PP2, or Flutec PC2; perfluoromethylcyclopentane, available from the same company under the trade name Flutec PC1C; and perfluorohexane and perfluorodimethylcyclohexane, available from the same company under the trade names Flutec PC1 and Flutec PC3, respectively. Perfluorodimethylcyclopentane (molecular weight of about 350) is also expected to be suitable in the present invention.

Colorant

An optional component of the post-application expanding composition of the present invention is a colorant, preferably a pigment.

The novel cosmetic composition of the present invention can be transparent or colored. Preferably, when it is to be applied to the eyelashes, it is colored. Prior art post-foaming gels have included colorants as an optional ingredient to give the composition a pleasing appearance. The composition of the present invention, optionally, incorporates one or more colorants in an amount sufficient to mask the color of the foam, which is usually white, so that when the composition of the present invention is applied to the hair, it imparts a color thereto other than white. Naturally, with white hair, a colorant need not be employed. When the composition of the present invention contains, for example pigment in an amount sufficient to mask the color of the foam and impart a color to keratin fibers treated with the composition, the composition of the invention can be used as a mascara, a hair-volumizing dye or colorant or an eyebrow composition, among others.

Virtually any level of colorant, preferably pigment, can be used so long as it substantially alters (preferably masks) the color of the foam that is otherwise produced on the hair absent the colorant. Preferably the colorant, preferably pigment(s), is present in an amount sufficient to impart a color to the hair fiber on which it is applied. The post-application expanding composition of the invention generally includes about 0.5 to about 30% by weight, preferably about 1 to 15% by weight, and more preferably about 2 to about 10% by weight, colorant, preferably pigment, based upon the total weight of the post-application expanding composition.

Thus, the post-application expanding composition of the present invention preferably includes, as a component, a colorant, preferably a pigment, most preferably a pigment dispersion containing one or more film forming agents, which are preferably film forming polymers. The pigment dispersion is preferred because of the physical attributes associated with a finely dispersed, clump free, color solution providing added film forming capability. A material that is particularly preferred, since it performs extremely well, is the material WSJ24BAMP available from Kobo Products. This material is comprised of water (43 to 50%, by weight); ethylmethacrylate/N-butylacrylate/2-methylhexyl acrylate copolymer (25 to 30%, by weight); iron II, III oxide (22 to 26% by weight); sodium acryloldimethyl taurate copolymer (0.1 to 5%, by weight); 2-amino-2-methyl-1-propanol (0.1 to 5%, by weight); and, optionally, a preservative blend (0.1 to 1%, by weight). Powdered pigments (Iron II, III oxide) may also be utilized and, when combined with the proper water-soluble polymeric film forming agents and properly dispersed, can accomplish the desired effect. WSJ24BAMP, the preferred material, is generally employed in an amount of from about 5 to about 50% by weight, based on the total weight of the post-application expanding composition. It should be appreciated that in lieu of the about 0.5 to about 30% by weight of pigment, the post-application expanding composition can contain from about 0.5 to about 90% by weight of a pigment dispersion comprised of polymeric film forming agents, pigment, emulsifier and other adjuvants.

Optional Ingredients

The post-application expanding composition of the present invention can optionally contain ingredients typically employed in cosmetics, provided they do not adversely affect the performance of the composition so as to prevent realization of its beneficial effects. Such additional ingredients include, for example, vitamins, antioxidants, preservatives, dyeing agents, fixative agents, styling agents and conditioning agents.

I. Solubilization System

When the post-application expanding composition of the present invention is based on a solubilization of the volatile agent it employs:

(1) an effective solubilizing amount, preferably about 0.5% to about 35%, more preferably about 5% to about 20%, by weight, based on the total weight of the post-application expanding composition, of a primary solubilizing agent for the volatile agent. The primary solubilizing agent is:

(A) at least one block polymer, preferably a block polymeric ether selected from the group consisting of:

(i) MEROXAPOL block polymer surfactants having the general formula:

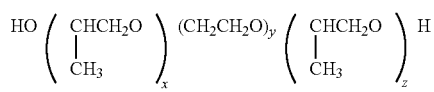

wherein
x has an average value of 7 to 21,
y has an average value of 4 to 16,
and z has an average value of 7 to 21, and x equals z.

Suitable MEROXAPOL block polymer surfactants include, MEROXAPOL 105, 108, 171, 172, 174, 178, 251, 252, 254, 255, 258, 311, 312, and 314. (see The Cosmetic Toiletry and Fragrance Association, International Cosmetic Ingredient Dictionary and Handbook, Vol. 2, 9$^{th}$ Edition, 2002, pp. 959-961.) Preferred MEROXAPOL block polymers include the PLURONIC R series (available from BASF);

(ii) POLOXAMER block polymer surfactants having the general formula:

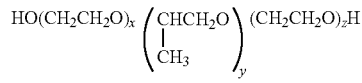

wherein
x has an average value of 2 to 128,
y has an average value of 16 to 67,
and z has an average value of 2 to 128, and x equal z.

Suitable POLOXAMER block polymer surfactants include: POLOXAMER 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, 407, POLOXAMER 105 benzoate and POLOXAMER 182 dibenzoate. (see The Cosmetic Toiletry and Fragrance Association, International Cosmetic Ingredient Dictionary and Handbook, Vol. 2, 9$^{th}$ Edition, 2002, pp. 1270-1275.) Preferred POLOXAMER block polymers include the PLURONIC L series (available from BASF);

and (iii) POLOXAMINE block polymer surfactants having the general formula:

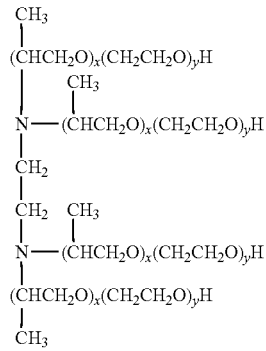

wherein x is 4 to 32,
and y is 2 to 122.

Suitable POLOXAMINE block polymers surfactants include: POLOXAMINE 304, 504, 604, 701, 702, 704, 707, 901, 904, 908, 1101, 1102, 1104, 1301, 1302, 1304, 1307, 1501, 1502, 1504, and 1508. (see The Cosmetic Toiletry and Fragrance Association, International Cosmetic Ingredient Dictionary and Handbook, Vol. 2, 9$^{th}$ Edition, 2002, pp. 1275-1279.) Preferred POLOXAMER block polymers include the TETRONIC series (available from BASF);

(B) Polyvinyl alcohol; or a polyvinyl alcohol alternative selected from the group consisting of: PEG-800/polyvinyl alcohol copolymer, sodium MA/vinyl alcohol copolymer, acetylated polyvinyl alcohol, vinylamine/vinyl alcohol copolymer, VP/VA copolymer, polyvinyl acetate and polyvinylacetal diethylaminoacetate. PEG-800/polyvinyl alcohol copolymer, sodium MA/vinyl alcohol copolymer, acetylated polyvinyl alcohol, vinylamine/vinyl alcohol copolymer and VP/VA copolymer are preferred polyvinyl alcohol alternatives; or (C) a mixture thereof.

(2) 0% to 25%, preferably about 0.5% to about 20%, more preferably about 0.75% to about 15%, most preferably about 1% to about 10%, by weight, based on the total weight of the post-application expanding composition, of a secondary solubilizer for the volatile agent. The secondary solubilizing agent is preferably an ammonium cocoyl isethionate selected from the group consisting of sodium oleoyl ammonium cocoyl isethionate, sodium myristoyl ammonium cocoyl isethionate, sodium lauroyl ammonium cocoyl isethionate, sodium cocoyl ammonium cocoyl isethionate, ammonium cocoyl isethionate and mixtures thereof. Sodium cocoyl ammonium cocoyl isethionate and ammonium cocoyl isethionate are preferred.

(3) about 0% to about 20%, preferably about 0.1% to about 15%, more preferably about 1% to about 10%, most preferably about 2% to about 5%, by weight, based on the total weight of the post-application expanding composition, of an anionic surfactant, preferably a salt of a $C_8$ to $C_{22}$ fatty acid, more preferably a salt of a $C_{10}$ to $C_{18}$ fatty acid, and most preferably a triethanolamine or alkali metal salt of palmitic acid or stearic acid; the salt being employed as such, or generated in situ in the post-application expanding composition by, for example, the reaction of the fatty acid and triethanolamine.

The combination of surfactants is employed in an amount sufficient to solubilize the volatile (blowing) agent component of the post-application expanding composition in the composition, thereby obviating the necessity for storing the composition in a pressurized container;

(4) 0% to about 20%, preferably about 0.1% to about 15%, more preferably about 1% to about 10%, most preferably about 2% to about 5% of an amphoteric or zwitterionic surfactant. Amphocarboxylates, alkyl betaines, amidoalkyl betaines, amidoalkyl sultaines, amphophosphates, phosphobetaines, pyrophosphobetaines, carboxyalkyl alkyl polyamines, alkyl amino monoacetates, alkyl amino diacetates, and mixtures thereof can be employed. Betaine surfactants are preferred. Cocamidopropyl betaine is most preferred;

(5) about 0.5% to about 20%, preferably about 1% to about 10% by weight, based on the total weight of the post-application expanding composition, of a volatile (blowing) agent. Suitable volatile (blowing) agents include any organic volatile (halogenated or non-halogenated) with a vapor pressure from about 0.5 Torr to about 30,000 Torr at a temperature of about 0° C. to about 100° C. Examples of preferred organic volatile agents include, but are not limited to, n-pentane, isopentane, n-butane, isobutane, isobutene, neopentane, cyclopentane, hexane, trichlorotrifluoroethane, 1,2-dichloro, 1,1,2,2-tetrafluoroethane, and mixtures thereof. Preferably, the volatile (blowing) agent is selected from the group consisting of n-pentane, isopentane, n-butane, isobutane, isobutene, neopentane, cyclopentane, hexane, and mixtures thereof;

(6) a film-forming agent in an amount effective to entrap at least a portion of foam produced by interaction of the surfactants(s), the solvent for the surfactant(s), and the volatile (blowing) agent, which occurs when the volatile (blowing) agent is released from the post-application expanding composition of the invention;

(7) 0% to about 5%, preferably about 0.5% to about 4%, more preferably about 0.75% to about 3%, most preferably about 1% to about 2%, by weight, based on the total weight of the post-application expanding composition, of an emollient selected from the group consisting of ethylhexyl hydroxystearate, ethylhexyl stearate, butylenes glycol stearate, $C_{12-15}$ alkyl benzoate, $C_{12-13}$ alkyl lactate, caprylic/capric glycerides, castor/olive oil esters, cetearyl ethylhexanoate, cetyl oleate, cocoglycerides, cyclomethicone, cyclopentasiloxane, dimethiconol, dimethicone PEG-7 isostearate, ethylhexyl isostearate, ethylhexyloxyglyceryl palmitate, ethylhexyl palmitate, glyceryl palmitate, hydrogenated polydecene, hydrogenated polyisobutene, isodecyl stearate, isopropyl palmitate, lanolin, mineral oil, PEG-11 cocoa butter glycerides, and mixtures thereof. Octylhydroxy stearate is most preferred;

(8) optionally, a colorant, preferably a pigment, more preferably a pigment dispersion, in an amount sufficient to impart a color other than white to hair fibers of the scalp, eyebrows or eyelashes. Liquid pigment dispersions containing film-forming polymers are preferred. The most preferred pigment dispersion is WSJ24BAMP. It is preferably used in an amount of about 5% to about 50%, more preferably, about 10% to about 40%, most preferably, about 20% to about 35%, by weight, based on the total weight of the post-application expanding composition.

As used herein "an effective solubilizing amount" or "an amount sufficient to solubilize" means an amount sufficient to prevent any significant separation of the volatile agent from the composition. Thus, for example, an effective solubilizing amount will substantially prevent the formation of a separate layer of the volatile agent. Typically, an effective solubilizing amount will be from about 0.5% to about 20%, preferably about 5% to about 10% by weight, based on the total weight of the final composition. Higher amounts can be employed but are likely to be economically unfeasible.

It should be noted that a particularly preferred Solubilization System employs a triblock copolymer surfactant and polyvinyl alcohol or an ammonium cocoyl isethionate. A more preferred Solubilization System employs a triblock copolymer surfactant, an ammonium cocoyl isethionate, such as sodium or ammonium cocoyl isethionate, and polyvinyl alcohol.

The following examples are provided solely for the purpose of illustrating the present invention and are not intended to limit the invention in any respect.

EXAMPLES 1-4

Mascara Formulations

| Ingredient | Ex. 1 wt. % | Ex. 2 wt. % | Ex. 3 wt. % | Ex. 4 wt. % |
| --- | --- | --- | --- | --- |
| Ethylhexyl hydroxy stearate | 1.0 | 1.0 | 1.0 | 1.0 |
| Oleth-3 phosphate | 0.5 | 0.5 | 0.5 | 0.5 |
| Isoceteth-20 | 0.5 | 0.5 | 0.5 | 0.5 |
| Palmitic acid | 3.0 | 3.0 | 3.0 | 3.0 |
| Stearic acid | 1.0 | 1.0 | 1.0 | 1.0 |
| Triethanolamine 99% | 1.5 | 1.5 | 1.5 | 1.5 |
| SYNTRAN EX-100 | 18.0 | 18.0 | 7.5 | 7.5 |
| PLURONIC block copolymer | 5.0 | 5.0 | 10.0 | 10.0 |
| Ammonium cocoyl isethionate | 3.0 | 3.0 | 5.0 | 5.0 |
| DAITOSOL 5000 SJ | 5.0 | 10.0 | 12.0 | 12.0 |
| WSJ24BAMP | 30.0 | 30.0 | 30.0 | 30.0 |
| Isopentane | 3.0 | 3.0 | 3.0 | 3.0 |
| LIQUAPAR | 0.5 | 0.5 | 0.5 | 0.5 |
| Gum arabic | 0.5 | 0.5 | 0.5 | 0.5 |
| Distilled water | 27.5 | 22.5 | 24.0 | 24.0 |

The compositions of Examples 1 to 4 are prepared according to the following general procedure:

(a) The SYNTRAN EX-100, DAITOSOL 5000 SJ, LIQUAPAR and WSJ24BAMP are mixed at room temperature.

(b) The triethanolamine, isoceth-20, oleth-3 phosphate, palmitic acid, stearic acid, ethylhexyl hydroxy stearate, gum arabic and water are mixed at a temperature of about 75° C. to about 80° C. then permitted to cool to room temperature.

(c) The ammonium cocyl isethionate and the PLURONIC block polymer are mixed with the aid of a flat propeller. The isopentane is added and the mixture is quickly and thoroughly mixed.

(d) The mixture of step (a) is added to the mixture of step (c) and thoroughly admixed therewith.

(e) The mixture of step (b) is then added to the mixture produced in step (d) and thoroughly admixed therewith. The resultant mixture is then transferred to a container fitted with an appropriate closure. In step (c), once the isopentane is added, the manufacturing process should be completed as quickly as possible.

It should be noted that in each of Examples 1-4 the block copolymer and ammonium cocoyl isethionate are principally employed for solubilization of the volatile agent (isopentane). The block copolymer functions as the primary solubilizing agent and the ammonium cocoyl isethionate functions as the secondary solubilizing agent. When the composition is spread on hair fibers, such as the eyelashes, the surface exposed to ambient conditions is increased. The volatile agent will then interact with the block copolymer and ammonium cocoyl isethionate and water to produce foam. Preferably additional surfactant(s) (for example, triethanolamine stearate and palmitate which are produced in situ) are employed to boost and stabilize foam production.

EXAMPLES 5-9

| Ingredient | Ex. 5 wt. % | Ex. 6 wt. % | Ex. 7 wt. % | Ex. 8 wt. % | Ex. 9 wt. % |
|---|---|---|---|---|---|
| Hydroxyethylcellulose | 0.5 | 0.75 | 0.75 | 0.75 | 0.75 |
| Polyvinyl alcohol | 10.0 | 5.0 | 5.0 | 5.0 | 5.0 |
| Triethanolamine 99% | 1.5 | 1.0 | 1.0 | 1.0 | 1.0 |
| Oleth-3 | 0.5 | 0.5 | 0.5 | 0.5 | 0.5 |
| Isoceteth-20 | 0.5 | 0.5 | 0.5 | 0.5 | 0.5 |
| Palmitic acid | 3.0 | 3.0 | 3.0 | 3.0 | 2.0 |
| Ethylhexyl hydroxy stearate | 2.0 | 1.75 | 1.75 | 1.75 | 2.25 |
| WSJ24BAMP | 25.0 | 30.0 | 30.0 | 30.0 | 25.0 |
| GERMABEN II | 0.5 | — | — | — | — |
| LIQUIPAR | — | 0.5 | 0.5 | 0.5 | 0.5 |
| E-14 film former | — | 15.0 | — | — | 10.0 |
| A-15 film former | — | — | 15.0 | — | — |
| ALLIANZ film former | — | — | — | 15.0 | — |
| Ammonium cocyl isethionate | 1.0 | 3.0 | 3.0 | 3.0 | 1.5 |
| Block copolymer 31R1 | 4.0 | 5.0 | 5.0 | 5.0 | 3.0 |
| Isopentane | 3.0 | 3.0 | 3.0 | 3.0 | 2.0 |
| Water | 48.5 | 31.0 | 31.0 | 31.0 | 46.0 |

EXAMPLES 10-16

| Ingredient | Ex. 10 wt. % | Ex. 11 wt. % | Ex. 12 wt. % | Ex. 13 wt. % | Ex. 14 wt. % | Ex. 15 wt. % | Ex. 16 wt. % |
|---|---|---|---|---|---|---|---|
| Octyl hydroxy stearate | 1.75 | 1.75 | 1.75 | 1.75 | 1.75 | 1.75 | 1.75 |
| Oleth-3 phosphate | 0.5 | 0.5 | 0.5 | 0.5 | 0.5 | 0.5 | 0.5 |
| Isoceteth-20 | 0.5 | 0.5 | 0.5 | 0.5 | 0.5 | 0.5 | 0.5 |
| Palmitic acid | 3.0 | 3.0 | 3.0 | 3.0 | 3.0 | 3.0 | 3.0 |
| Triethanolamine 99% | 1.0 | 1.0 | 1.0 | 1.0 | 1.0 | 1.0 | 1.0 |
| PLURONIC block copolymer 31R1 | 5.0 | 5.0 | 5.0 | 5.0 | 5.0 | 5.0 | 5.0 |
| PLURONIC block copolymer L-61 | | | | 5.0 | | | 5.0 |
| Ammonium cocyl isethionate | 3.0 | 3.0 | 3.0 | 3.0 | 3.0 | 3.0 | 3.0 |
| Allianz OPT (ISP) | 10.0 | 5.0 | — | 10.0 | 5.0 | — | 10.0 |
| Polyvinyl alcohol | 10.0 | 10.0 | 10.0 | 10.0 | 10.0 | 10.0 | 10.0 |
| Johnson polymer EPQ30 | 5.0 | 5.0 | 10.0 | — | 5.0 | 10.0 | — |
| WSJ24BAMP | 30.0 | 30.0 | 30.0 | 30.0 | 30.0 | 30.0 | 30.0 |
| Isopentane | 3.00 | 3.00 | 3.00 | 3.00 | — | — | — |
| n-Pentane | — | — | — | — | 3.00 | — | — |
| Cyclopentane | — | — | — | — | — | 5.00 | — |
| Cyclopentane/Isopentane (1:1 ratio) | — | — | — | — | — | — | 3.00 |
| LIQUAPAR | 0.50 | 0.50 | 0.50 | 0.50 | 0.50 | 0.50 | 0.50 |
| Sodium carboxymethyl cellulose | 0.75 | 0.75 | 0.75 | 0.75 | 0.75 | 0.75 | 0.75 |
| Distilled water | 26.0 | 31.0 | 31.0 | 31.0 | 31.0 | 29.0 | 31.0 |

A composition, such as the composition of Examples 5 to 16, may be made according to the procedure of Example 17 which follows. Although the process of Example 17 employs a specified formulation in order to exemplify the process, other compositions of the invention employing a block polymer can be similarly prepared.

EXAMPLE 17

Typical Method of Manufacture

| Phase | Ingredient | wt. % |
|---|---|---|
| A | Deionised Water (DM) | 31 |
| A | Sodium carboxymethylcellulose | 0.75 |
| A | Polyvinyl alcohol | 10 |
| A | Triethanolamine (TEA) | 1.5 |
| B | Oleth-3-phosphate | 0.5 |
| B | Isoceteth-20 | 0.5 |
| B | Ethylhexyl hydroxyl stearate | 1.25 |
| B | Palmitic acid | 3 |

-continued

| Phase | Ingredient | wt. % |
|---|---|---|
| C | ALLIANZ OPT | 10 |
| C | EPQ 30 POLYURETHANE | 5 |
| D | WSJ24BAMP | 25 |
| E | LIQUAPAR | 0.5 |
| F | PLURONIC Block Polymer | 5 |
| F | Ammonium cocoyl ammonium cocoyl isethionate | 3 |
| F | Isopentane | 3 |

Procedure:
(a) sprinkle the sodium carboxymethylcellulose into the water under medium/slow (400-600 rpm) tripleL blade mix. Allow the sodium carboxymethyl cellulose to fully disperse with no clumps;
(b) add the polyvinyl alcohol slowly and allow adequate time for its dispersal;
(c) add the triethanolamine and cover and heat phase A to 75° C.;
(d) At 75° C. add phase B ingredients allowing about 3-5 minutes between each addition so as to permit each ingredient to fully mix/disperse before adding the next;
(e) mix the combined phases A and B at 75° C. for about 10 minutes;
(f) discontinue heating and cool to about 55° C., replace the propeller with a waffle iron sweep and continue to sweep at 80 to 100 rpm;
(g) at 55° C., slowly add phase C directly into the batch. Mix for five minutes;
(h) cool to about 45° C., add phase D slowly under sweep mixing. Use a spatula to scrape the sides of the vessel and ensure a thorough mix;
(i) at about 30° C., add phase E under sweep mixing;
(j) continue the sweep mixing and cooling until the composition reaches approximately 2° C. to about 5° C.;
(k) prepare phase E separately from the main composition and under cold conditions (approximately 2° C. to about 5° C.) (It should be noted that the processing temperature depends on the volatile agent used. With a more stable volatile agent a higher temperature can be employed);
(l) chill the block polymer and place it in a cold jacketed vessel, add the chilled volatile agent(s) and mix for about 10 minutes;
(m) slowly drizzle the ammonium cocoyl isethionate into the pentane/block polymer mix and continue mixing for about 5 minutes;
(n) using a large homogenizer, slowly add chilled phase E to the main batch (phases A, B, C, and D) and mix until phase E is fully dispersed; and
(o) charge the resultant mixture into a suitable vessel.

II. Microemulsion System

Microemulsions are thermodynamically stable isotropic dispersions of oil and water containing domains of nanometer dimensions stabilized by the interfacial film of surface-active agent(s). Essentially, a microemulsion is a multicomponent mixture formed of oil, water, surfactant, co-surfactant and electrolyte.

A major difference between a conventional mixture and a microemulsion is the former is mixed on a molecular scale, while in the latter, globules of oil or water on the order of 10-100 nm in diameter, are respectively dispersed as globules in water or oil. The surfactant and co-surfactant are mainly located at the interface between the two phases, as well as distributed, at equilibrium, between the two media. Depending upon the compositional makeup of the microemulsion, various phases and equilibria may be achieved. Some typical conformations may be oil-in-water (Winsor I), water-in-oil (Winsor II) and bicontinuous or layered (Winsor III).

The present inventors surprisingly found that a microemulsion's minute droplet size, and the thermodynamic stability that comes with such a system, acts to arrest a volatile (blowing) agent. Because the volatile agents are dispersed as nanometer sized droplets, a microemulsion system effectively reduces the vapor pressure associated with "neat" volatile (blowing) agents. Post-application expanding compositions that are microemulsion based are stable even though they contain a high load of volatile (blowing) agent.

The use of a microemulsion system as a base for the post-application expanding composition of the present invention, enables the production of, for example, a post-application expanding mascara that does not require packaging in a barrier type canister, such as a pressurized can.

When a post-application expanding composition, based on a microemulsion system in accordance with the present invention, is stored in a closed container, the volatile (blowing) agent contained in the post-application expanding composition is fully arrested. In other words, the volatile agent remains dispersed within the microemulsion. When the microemulsion based post-application expanding composition of the invention is removed from the container and applied to and spread over a surface, such as an eyelash, and the composition is exposed to normal atmospheric conditions, the volatile (blowing) agent will slowly migrate out of the composition as a gas and interact with the surfactant(s) and solvent for the surfactants(s) and create a foam lattice. This lattice can be further optimized using a foaming system such as a sodium salt of a fatty acid(s) and/or one or more foam boosters such as a betaine or sultaine. The lattice can be captured or held in the expanded configuration by using natural or synthetic film formers or a combination thereof.

The microemulsion may be tailored to give a multitude of product options such as low viscosity liquids, high viscosity liquids, gels, creams, semi-solids and even solids.

The following examples 18-22 serve to illustrate compositions of the present invention based on the Microemulsion System:

EXAMPLES 18-22

| Ingredient | Ex. 18 wt. % | Ex. 19 wt. % | Ex. 20 wt. % | Ex. 21 wt. % | Ex. 22 wt. % |
|---|---|---|---|---|---|
| Propylene glycol | 2.0 | 5.0 | 5.0 | 2.0 | 2.0 |
| Cyclomethicone | 15.0 | — | — | 24.5 | 22.0 |
| Isododecane | — | 5.0 | — | — | — |
| Silicone polyether | — | — | — | 10.5 | 12.5 |
| Oleth-3 phosphate | — | — | 5.0 | — | — |
| Oleth-10 | — | — | 2.0 | — | — |
| Palmitic acid | — | 2.5 | 1.5 | — | — |
| Cocamidopropyl betaine | 4.5 | 5.0 | 1.0 | 1.5 | 5.0 |
| Triethanolamine 99% | — | 1.0 | 0.5 | — | — |
| PPG-10 cetyl ether propylene glycol | 5.0 | — | — | — | — |
| PPG-5 ceteth-20 | 16.0 | — | — | — | — |
| Sodium lauryl ether sulfate-2EO | — | 10.0 | — | — | — |
| Isostearyl benzoate | 10.0 | — | — | — | — |
| Light mineral oil | — | — | 10.0 | — | — |
| ALLIANZE OPT | — | — | — | — | 10.0 |

-continued

| Ingredient | Ex. 18 wt. % | Ex. 19 wt. % | Ex. 20 wt. % | Ex. 21 wt. % | Ex. 22 wt. % |
|---|---|---|---|---|---|
| Polyvinyl alcohol | — | — | — | — | 10.0 |
| PVP | 1.0 | — | 2.0 | — | — |
| DAITOSOL 5000 SJ | 5.0 | 10.0 | 5.0 | 10.0 | — |
| SYNTRAN EX-100 | — | — | — | 7.5 | — |
| Iron oxide black (treated) | 6.0 | 5.0 | 5.0 | 5.0 | 6.0 |
| Isopentane | — | 6.0 | — | — | — |
| Cyclopentane | 10.0 | — | — | — | — |
| Cyclopentane/Isopentane (1:1 ratio) | — | — | 10.0 | 10.0 | — |
| n-pentane | — | — | — | — | 10.0 |
| Methylparaben | 0.3 | 0.3 | 0.3 | 0.3 | 0.3 |
| GERMALL | 0.2 | 0.2 | 0.2 | 0.2 | 0.2 |
| Sodium carboxymethyl cellulose | 0.25 | 0.2 | 0.5 | 0.2 | 0.5 |
| Distilled water | 24.75 | 49.8 | 52.0 | 24.5 | 21.5 |

III. Two Part System

When mixed with water, bicarbonates and carbonates can form carbonic acid and salts. Carbonic acid is unstable in water and at room temperature spontaneously rapidly breaks down into carbon dioxide gas and water. The chemistry involved is represented by the following reaction scheme

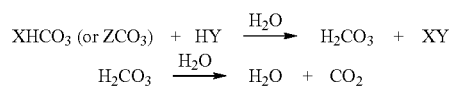

wherein

X is an alkali metal cation or an ammonium cation

Z is an alkaline earth metal cation

HY is a mineral or organic acid and XY is an alkali or alkaline earth metal salt More specifically, in this embodiment of the present invention, the volatile (blowing) agent, carbon dioxide, is generated, in situ, by the facile reaction of a cosmetically acceptable acid with a base, in the presence of water. The carbonic acid that is produced is unstable in water and breaks down at room temperature into water and carbon dioxide gas. The carbon dioxide foams (swells or expands) the composition.

Suitable acids include, but are not limited to, citric acid, boric acid, tartaric acid, succinic acid, malic acid, formic acid, glycolic acid, polyacrylic acid, polyaspartic acid and mixtures thereof. Microporous silica or a buffered mineral acid (such as hydrochloric acid or phosphoric acid) having a pH of 5 or less can also be employed. Citric acid is preferred.

Suitable bases include, but are not limited to, (i) inorganic carbonates and bicarbonates, for example, ammonium, alkali metal and alkaline earth metal carbonates and bicarbonates, and (ii) organic carbonates, such as diethyl carbonate, propylene carbonate and dipropyl carbonate. Magnesium carbonate, calcium carbonate, sodium bicarbonate, sodium carbonate, diethyl carbonate, propylene carbonate and dipropyl carbonate are preferred. Sodium and potassium bicarbonate are most preferred.

When a polyacrylic acid is employed as the acid reaction component the expansion caused by the release of carbon dioxide can be controlled by (i) increasing the pH, which serves to thicken the polymer film and/or by (ii) increasing the amount of water in the composition, which serves to retard the reaction.

To apply this chemistry to a post-application expanding composition, for application to the hair of the scalp, eyebrows or eyelashes, the water must be kept from the bicarbonate or carbonate and acid until the in-situ formation of carbon dioxide gas is to take place.

A preferred embodiment for employing in situ generated carbon dioxide utilizes a two part composition. Each part is packaged in different chambers of a single two chambered container or the two parts are packaged in separate containers.

For example, citric acid is dispersed in the anhydrous post-application expanding composition of the present invention and the mascara is applied to, for example, the eyelashes. Simultaneously, or shortly thereafter, an aqueous solution of a cosmetically acceptable base, such as sodium bicarbonate, is applied to the eyelashes and mixed with the mascara with the aid of a mascara brush whereupon carbon dioxide evolves. The carbon dioxide foams (swells or expands) the surfactant and solvent for the surfactant components of the post-application expanding composition. The film-forming agent component of the composition thereafter sets and entraps at least a portion of the produced foam so as to fix the composition in an expanded state.

Alternatively, anhydrous sodium bicarbonate and anhydrous acid are dispersed in an anhydrous mascara composition and the composition is mixed on the eyelashes with an aqueous composition containing the surfactant. A mascara brush is employed to mix the aqueous surfactant solution with the mascara containing the sodium bicarbonate and acid. The surfactant facilitates mixing and the carbon dioxide that is produced acts to foam the surfactant and solvent for the surfactant. When the film-forming agent component, preferably present in the aqueous solution, sets it entraps at least a portion of the produced foam lattice and fixes the post-application expanding composition in an expanded state.

Water must be kept from the bicarbonate or carbonate and acid until it is desired that the in-situ formation of carbon dioxide gas take place.

For example, in the case of a mascara composition, a two part mascara would be formulated. Each part would be packaged in different chambers of a single container or two separate containers can be used. The formulation amount of water (generally greater than 40 wt. %, based on the total weight of the final composition) present in one part of the composition is packaged in one of the chambers (or in one of the separate containers). The other chamber (or other separate container) contains the anhydrous part of the formulation. The anhydrous part would be applied to the eyelashes first, followed by the aqueous part. The surfactants(s) present in the formulation coupled with mechanical action of the mascara brush will facilitate mixing of the two parts and the in-situ production of carbon dioxide.

In a preferred embodiment of the present invention a first part of the post-application expanding composition, containing the carbonate or bicarbonate and the acid dissolved or dispersed in anhydrous polyethylene glycol is stored in one compartment of a dual compartment container. A second part of the post-application expanding composition, containing the formulation amount of water, is stored in the other compartment.

Alternatively, one part is stored in a first container and the other part is stored in a second container. The surfactant(s) and film-forming agent can be components of the aqueous part of the composition.

The acid and base can be dispersed in an anhydrous water-miscible vehicle or the acid can be contained in the anhydrous water-miscible vehicle and the base contained in the aqueous part of the composition. The reverse (the acid in the aqueous part and the base in the anhydrous part) can lead to potential eye irritation, color instability and a change in viscosity.

Anhydrous polyethylene glycol is highly preferred as a vehicle for the carbonate or bicarbonate and the acid reactants. Its hygroscopicity promotes speedy in-situ production of carbon dioxide when the aqueous part of the composition is mixed with the anhydrous acid/base containing part of the composition. Although anhydrous, polyethylene glycol is preferred, any viscous anhydrous cosmetically acceptable solvent that is readily miscible with water and in which the anhydrous acid and base can be suspended without co-reacting, can be employed. Sorbitol and glycerin are additional examples of such solvents.

It should be noted that as an alternative to separating the acid and base reactants in separate compartments, one can encapsulate the base so as to physically separate it from the other reactant.

Stoichiometric amounts of the acid and base (carbonate or bicarbonate) reactants should be employed. The co-reactants should be employed in amounts such that, when reacted, sufficient carbon dioxide is produced to interact with the surfactant(s) and solvent for the surfactant(s) to produce sufficient foam lattice and expansion before the film forming agent sets.

The following examples are offered solely to illustrate two part compositions prepared in accordance with this embodiment of the present invention and are not intended to be limiting in any respect.

In each of Examples 23-25, which follows, Part B contains the bicarbonate/acid mixture and Part A contains the water. In Example 23, Part B is based on an oil gelled polymer. In Example 24, Part B is based on anhydrous polyethylene glycol 400. If a higher or lower viscosity product is desired, a higher or lower molecular weight polyethylene glycol, or mixture of polyethylene glycols can be employed. In Example 25; Part B is based on an emulsifying wax. Part A of Examples 23 and 24 have a high water content and low viscosity, such as is typically employed by mascara formulations. Part A of Example 25 contains black mica Consequently, the formulation of Example 25 is useful as an eyebrow tint.

EXAMPLE 23

| Ingredient | % |
| --- | --- |
| Part A | |
| Methylparaben | 0.4 |
| Hydroxethylcellulose HHR 250 | 0.1 |
| Propylene glycol | 4.0 |
| PVM/MA Copolymer | 1.0 |
| Black iron oxide/styrene acrylate treated | 7.0 |
| Kaolin | 1.0 |
| Sodium silicoaluminate | 0.1 |
| Glycerin | 1.0 |
| Acrylates copolymer aqueous/Butylene glycol | 10.0 |
| Biosaccharide Gum-1 | 1.0 |
| 2-Phenoxyethanol | 0.98 |
| Rose oil | 0.03 |
| Chroma-lite black | 2.0 |
| Colorona patina silver | 0.5 |
| Demineralized water | 70.89 |
| Part B | |
| Isododecane and ethylene/propylene/styrene copolymer and butylene/ethylene/styrene copolymer | 69.0 |

-continued

| Ingredient | % |
| --- | --- |
| Potassium bicarbonate/citric acid, powdered (18.4/11.6) | 30.0 |
| PEG-80 Sorbitan laurate/cocamide surfactant | 1.0 |

For Part A, the hydroxyethylcellulose is slowly dispersed in the water while vigorously stirring. The temperature is increased to 75° C. and the remainder of the ingredients are blended in. The batch is then slowly cooled to room temperature. The Part B ingredients are mixed at room temperature until the powdered potassium bicarbonate/citric acid mixture and surfactant are thoroughly dispersed in the mixture of isododecane and ethylene/propylene/styrene copolymer and butylene/ethylene/styrene copolymer.

EXAMPLE 24

| Ingredient | % |
| --- | --- |
| Part A | |
| PVP | 2.0 |
| Acacia senegal gum | 0.3 |
| Cellulose gum (2000 CPS) | 0.4 |
| Polyquaternium-10 | 0.3 |
| Methylparaben | 0.4 |
| Triethanolamine 99% | 1.6 |
| Iron oxides (black)/silica/BHT | 9.5 |
| Pentaerythritol tetrastearate | 1.0 |
| Shellac wax 100% | 3.0 |
| Carnauba wax | 1.8 |
| Beeswax | 5.2 |
| Paraffin wax 165 | 8.5 |
| Stearic acid | 4.0 |
| Isooctahexacontane | 2.5 |
| Glyceryl monostearate-self emulsifying | 2.0 |
| Silica-low absorbing | 2.0 |
| Propylparaben | 0.2 |
| Acrylates copolymer/Isododecane | 0.1 |
| Isododecane/gellants/BHT | 2.5 |
| Acrylates copolymer-30%/aqueous | 1.5 |
| Soybean oil | 0.1 |
| Hydrolyzed silk | 0.1 |
| Demineralized water | 51.0 |
| Part B | |
| PEG-400 | 69.0 |
| Potassium bicarbonate/citric acid, powdered (18.4/11.6) | 30.0 |
| PEG-80 Sorbitan laurate/cocamide surfactant | 1.0 |

For Part A, the cellulose gum is slowly dispersed in the water while vigorously stirring. The remainder of the ingredients (except the waxes) are blended in, with the triethanolamine added last, until the pH is measured as neutral. The temperature is increased to 75° C. Separately the waxes are melted and then milled into the batch. The batch is then slowly cooled to room temperature. The Part B ingredients are mixed at room temperature until the powdered potassium bicarbonate/citric acid mixture and surfactant are thoroughly dispersed in the PEG-400.

EXAMPLE 25

| Ingredient | % |
|---|---|
| Part A | |
| PVM/MA copolymer | 1.0 |
| Methylparaben | 0.4 |
| Imidazolidinyl urea | 0.2 |
| PVP/VA copolymer-50% aqueous | 30.0 |
| Propylene glycol | 4.0 |
| Glycerin | 1.0 |
| Alcohol SD 40B | 5.0 |
| Mica | 0.25 |
| PEG-80 Sorbitan laurate/cocamide | 1.0 |
| Black mica | 3.75 |
| Acrylates copolymer aqueous/butylenes glycol | 10.0 |
| Demineralized water | 43.4 |
| Part B | |
| Isododecane | 44.7 |
| Emulsifying wax | 30.3 |
| Potassium bicarbonate/citric acid, powdered (18.4/11.6) | 25.0 |

For Part A, the ingredients are blended in the water at 45° C. The batch is then slowly cooled to room temperature. The Part B ingredients are mixed at a temperature slightly above the melting point of the emulsifying wax until the powdered potassium bicarbonate/citric acid mixture is thoroughly dispersed in the mixture.

The following Examples 26 through 29 are illustrative of post-application expanding compositions that rely on mechanical agitation (rather than a volatile agent) for production of the foam lattice and consequently, do not require packaging in pressure resistant containers.

EXAMPLES 26-29

Mascara Formulations

| Ingredient | 26 wt. % | 27 wt. % | 28 wt. % | 29 wt. % |
|---|---|---|---|---|
| Hydroxyethyl cellulose | 0.5 | 0.5 | 0.5 | 1.0 |
| Oleth-3 phosphate | 0.5 | 0.5 | 0.5 | — |
| Isoceteth-20 | 0.5 | 0.5 | 0.5 | — |
| Palmitic acid | 4.0 | 2.0 | 4.0 | — |
| Triethanolamine 99% | 1.0 | 1.0 | 1.0 | — |
| SYNTRAN EX-100 | 10.0 | 11.0 | 18.0 | 18.0 |
| DAITOSOL 5000 SJ | 12.0 | 12.0 | 12.0 | 12.0 |
| Cocamidopropyl betaine | 0.5 | 0.5 | 3.0 | 4.0 |
| WSJ24BAMP | 25.0 | 25.0 | 25.0 | 25.0 |
| GERMABEN II | 0.5 | 0.5 | — | — |
| Sodium laureth sulfate | — | — | — | 2.0 |
| LIQUAPAR | — | — | 0.5 | 0.5 |
| Deionized water QS to | 100 | 100 | 100 | 100 |

The composition of the present invention when applied in the form of a mascara is advantageous in that much fewer brush stokes are required and thus manipulation is greatly reduced. For example, 3 to 5 brush stokes are required rather than the 14 or more brush stokes typically employed when mascara products of the prior art are applied to eyelashes.

The composition of the present invention can be used for hair volumizing and, consequently, can be used on the hair of the head, eyebrows and eyelashes. As noted earlier, when used for volumizing it can be employed with or without a colorant, such as a pigment.

When used on scalp hair that is white, no colorant is required. However, when used on hair that is other than gray or white, a colorant, such as a pigment, is generally included in the composition of the present invention. Sufficient colorant or pigment should be utilized to mask the color of the entrapped foam, preferably sufficient colorant should be employed to impart to the hair fibers a predetermined desired amount of color.

The present invention also includes a method of imparting volume to the hair of the scalp, eyebrows or eyelashes comprising applying the composition of the present invention to such hair.

The post-application expanding compositions of the present invention may be packaged in many types of commercially available containers, including collapsible metal tubes and barrier-type aerosol dispensers. If an aerosol dispenser is employed, it is preferred that the post-application expanding composition be maintained in the container separate from the propellant by means of a bag, diaphragm or piston inside the container. This propellant is not to be confused with the volatile (blowing) agent that is a component of the composition. If a diaphragm or piston is employed, it can be driven by propellant or mechanical force, such as a spring.

Compositions according to the present invention may be packaged in, for example, the packaging systems described in U.S. Pat. Nos. 2,995,521; 3,541,581; 3,654,167; 4,405,489; 4,528,111; 4,651,503; 6,165,456 and US Patent Application Publication US 2002/0122772 A1.

It should be understood that the foregoing description is only illustrative of some embodiments of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A method for imparting a volumizing effect to eyelashes comprising the step of contacting the eyelashes with a post-expanding composition comprising a film-forming agent, a surfactant, a solvent for the surfactant, and a volatile agent, wherein the film-forming agent is present in an amount effective to form a film that entraps at least a portion of foam formed by interaction of the volatile agent and the surfactant after the composition is applied to a hair fiber, the volatile agent being solubilized in the composition by a solubilizing agent selected from the group consisting of a block polymer surfactant, a polyvinyl alcohol-containing polymer surfactant, and a mixture thereof, wherein the solubilizing agent is present in an amount sufficient to prevent separation of the volatile agent from the composition whereby the composition is storable in a non-pressurized container.

2. The composition of claim 1, wherein the composition includes about 1 to about 50% by weight of the film-forming agent, based on the total weight of the composition.

3. The composition of claim 1, wherein the composition includes about 5 to about 40% by weight of the film-forming agent, based on the total weight of the composition.

4. The composition of claim 1, wherein the composition includes about 8 to about 30% by weight of the film-forming agent, based on the total weight of the composition.

5. The composition of claim 1, wherein the composition includes about 10 to about 25% by weight of the film-forming agent, based on the total weight of the composition.

6. The composition of claim 1, wherein the film-forming agent is a polymer.

7. The composition of claim 1, wherein the film-forming agent is a copolymer.

8. The composition of claim 7, wherein the film-forming agent is selected from the group consisting of an acrylates copolymer, methacrylates copolymer, acrylamides copolymer, and mixtures thereof.

9. The composition of claim 1, wherein the composition contains a colorant.

10. The composition of claim 9, wherein the colorant is a pigment.

11. The composition of claim 10, wherein the pigment is a pigment dispersion.

12. The composition of claim 11, wherein the pigment dispersion comprises water, an iron oxide and a second film forming agent.

13. The composition of claim 1, wherein the composition contains a water-soluble viscosity increasing agent.

14. The composition of claim 13, wherein the water-soluble viscosity increasing agent is selected from the group consisting of synthetic sucrose derivatives, cellulose gums and hydrophilic colloids.

15. The composition of claim 1, wherein the composition contains a block polymeric ether selected from the group consisting of MEROXAPOL block polymer surfactants, POLOXAMER block polymer surfactants, and POLOXAMINE block polymer surfactants, and the block polymeric ether is present in an amount sufficient to solubilize the volatile agent in the composition.

16. The composition of claim 1, wherein the composition contains an anionic surfactant.

17. The composition of claim 16, wherein the anionic surfactant is selected from the group consisting of water-soluble salts of $C_{10}$ to $C_{22}$ fatty acids, alkyl sulfates, alkyl ether sulfates, alkyl monoglyceryl ether sulfates, alkyl monoglyceride sulfates, alkyl monoglyceride sulfonates, alkyl sulfonates, alkylaryl sulfonates, alkyl sulfosuccinates, alkyl ether sulfosuccinates, alkyl sulfosuccinates, alkyl amidosulfosuccinates, alkyl carboxylates, alkyl amidoethercarboxylates, alkyl succinates, fatty acyl sarcosinates, fatty acyl amino acids, fatty acyl taurates, fatty alkyl sulfoacetates, alkyl phosphates, alkyl ether phosphates, and mixtures thereof.

18. The composition of claim 17, wherein the water-soluble salts of $C_{10}$ to $C_{22}$ fatty acids are selected from the group consisting of sodium, potassium and triethanolamine salts of palmitic acid, stearic acid, oleic acid, myristic acid, palm and coconut oil fatty acids, and mixtures thereof.

19. The composition of claim 1, wherein the composition contains an amphoteric or zwitterionic surfactant.

20. The composition of claim 19, wherein the amphoteric or zwitterionic surfactant is selected from the group consisting of amphocarboxylates, alkyl betaines, amidoalkyl betaines, amidoalkyl sultaines, amphophosphates, phosphobetaines, pyrophosphobetaines, carboxyalkyl alkyl polyamines, alkyl amino monoacetates, alkyl amino diacetates, and mixtures thereof.

21. The composition of claim 1, wherein the composition contains a nonionic surfactant.

22. The composition of claim 21, wherein the nonionic surfactant is a polyoxyethylene derivatives of a polyol ester.

23. The composition of claim 2, wherein the volatile agent has a vapor pressure from about 0.5 Torr to about 30,000 Torr, at a temperature of about 0° to about 100° C.

24. The composition of claim 23, wherein the vapor pressure is from about 5.0 Torr to about 5,000 Torr.

25. The composition of claim 23, wherein the vapor pressure is from about 100 Torr to about 2,500 Torr.

26. The composition of claim 1, wherein the volatile agent is selected from the group consisting of n-pentane, isopentane, neopentane, n-butane, isobutane, isobutene, cyclopentane, hexane, trichlorotrifluorethane, 1,2-dichloro, 1,1,2,2-tetrafluoroethane, hydrofluoroethers and mixtures thereof.

27. The composition of claim 1, wherein said solubilizing agent is selected from the group consisting of a block polymer surfactant, polyvinyl alcohol-containing polymer surfactant, and a mixture thereof.

28. The composition of claim 27, wherein said solubilizing agent is a block polymer surfactant.

29. The composition of claim 26, wherein said volatile agent is selected from the group consisting of isopentane, n-butane, isobutane, and mixtures thereof.

30. The composition of claim 29, wherein said volatile agent is isopentane.

* * * * *